(12) United States Patent
Zhou et al.

(10) Patent No.: US 6,767,912 B2
(45) Date of Patent: Jul. 27, 2004

(54) HETEROCYCLYLINDAZOLE AND -AZAINDAZOLE COMPOUNDS AS 5-HYDROXYTRYPTAMINE-6 LIGANDS

(75) Inventors: Ping Zhou, Plainsboro, NJ (US); Derek Cecil Cole, New City, NY (US); Michael Gerard Kelly, Thousand Oaks, CA (US); William Joseph Lennox, Monsey, NY (US)

(73) Assignee: Wyeth, Madison, NJ (US)

( * ) Notice: Subject to any disclaimer, the term of this patent is extended or adjusted under 35 U.S.C. 154(b) by 91 days.

(21) Appl. No.: 10/028,168

(22) Filed: Dec. 20, 2001

(65) Prior Publication Data

US 2002/0198213 A1 Dec. 26, 2002

Related U.S. Application Data

(60) Provisional application No. 60/257,627, filed on Dec. 22, 2000.

(51) Int. Cl.$^7$ .................... A61K 31/437; A61K 31/416; A61K 31/404; C07D 403/04; C07D 471/04; A61P 25/00
(52) U.S. Cl. .................... 514/300; 514/403; 514/415; 514/370; 514/314; 514/217.08; 514/217.05; 514/323; 546/113; 546/172; 546/119; 546/201; 548/362.5; 548/361.1; 548/466; 548/181; 540/599; 540/602; 540/603
(58) Field of Search .................... 546/113, 172; 548/362.5, 361.1, 466, 181; 514/300, 403, 415, 370, 314

(56) References Cited

U.S. PATENT DOCUMENTS

| | | | |
|---|---|---|---|
| 5,409,941 A | 4/1995 | Nowakowski | |
| 6,066,637 A | 5/2000 | Kelly et al. | |
| 6,133,287 A | 10/2000 | Slassi et al. | |
| 6,143,744 A | 11/2000 | Broka et al. | |
| 6,191,141 B1 | 2/2001 | Edwards et al. | |

FOREIGN PATENT DOCUMENTS

| | | | |
|---|---|---|---|
| WO | WO 98/23587 A | 6/1998 | |
| WO | WO 99/65906 A1 | 12/1999 | |
| WO | WO 00/63203 A | 10/2000 | |

OTHER PUBLICATIONS

Julia M and Bagot J. Bull. Soc. Chim. France (1964), 8, 1924–38.*

Zheng, Q. et al., Palladium catalyzed cross–coupling reaction between 3–indole boronic acids and tetrahydropyridine triflates, Tetrahedron Letters, 1993, vol. 34(14), 2235–2238, Elsevier Science Publishers, Amsterdam, NL.

Zheng, Q. et al., Vinylation of the indole 3–position via palladium–catalyzed cross–coupling, Heterocycles, 1994, vol. 37(3), 1761–1772.

Schut, R. N. et al., 2–Tetrahydropyridylindoles as histamine and serotonin antagonists, Journal of Medicinal Chemistry, 1970, vol. 13(3), 394–397.

Busacca, C. A., et al., A facile synthesis of 4–Aryl–2, 3–Dihydropyrroles, Tetrahedron Letters, 1996, vol. 37(23), 3947–3950, Elsevier Science Publishers, Amsterdam, NL.

Sleight, et al., The 5–hydroxytryptamine–6 receptor: localisation and function, Expert Opinion on Therapeutic Patents, 1998, vol. 8(10), 1217–1224, Ashley Publications, GB.

* cited by examiner

Primary Examiner—Evelyn Mei Huang
(74) Attorney, Agent, or Firm—Barbara L. Lences

(57) ABSTRACT

The present invention provides a compound of formula I and the use thereof in the therapeutic treatment of disorders related to or affected by the 5-HT6 receptor.

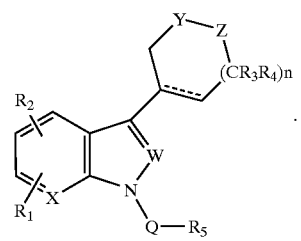

(I)

17 Claims, No Drawings

HETEROCYCLYLINDAZOLE AND -AZAINDAZOLE COMPOUNDS AS 5-HYDROXYTRYPTAMINE-6 LIGANDS

This application claims priority from application Serial No. 60/257,627 filed on Dec. 22, 2000, the entire disclosure of which is incorporated by reference.

BACKGROUND OF THE INVENTION

A number of central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include 5-HT1, 5-HT2, 5-HT3, 5-HT4, 5-HT5, 5-HT6 and 5-HT7 subtypes.

The recently identified human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Northern blots have revealed that 5-HT6 receptor mRNA appears to be exclusively present in the brain, with little evidence for its presence in peripheral tissues.

The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Compounds which interact with, stimulate or inhibit the 5-HT6 receptor are commonly referred to as 5-HT6 ligands. These 5-HT6 receptor ligands are believed to be of potential use in the treatment of a variety of central nervous system disorders such as anxiety, depression, epilepsy, obsessive-compulsive disorders, migraine, cognitive disorders, sleep disorders, feeding disorders, panic attacks, disorders relating to withdrawl from drug abuse, schizophrenia, or the like or in the treatment of certain gastrointestinal disorders such as irritable bowel syndrome.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a compound of formula I wherein

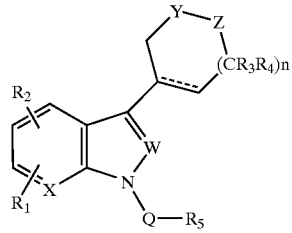

$Q$ is $SO_2$, CO, $CONR_{24}$, $CSNR_{25}$ or $CH_2$;

$W$ is N or $CR_6$;

$X$ is N or $CR_7$;

$Y$ is $NR_8$ or $CR_9R_{10}$;

$n$ is 0 or an integer of 1 or 2;

$Z$ is $NR_{11}$ or $CR_{12}R_{13}$ with the proviso that when $n$ is 1, $Q$ is $SO_2$, CO or $CH_2$, and $W$ is $CR_6$ then $Z$ must be $CR_{12}R_{13}$ and with the further provisos that when $Y$ is NR8 then $Z$ must be $CR_{12}R_{13}$ and at least one of $Y$ and $Z$ must be NR8 or $NR_{11}$;

$R_1$, $R_2$ and $R_7$ are each independently H, halogen, CN, $OCO_2HR_{14}$, $CO_2R_{15}$, $CONR_{29}R_{30}$, $CNR_{16}NR_{17}R_{18}$, $SO_mR_{19}$, $NR_{20}R_{21}$, $OR_{22}$, $COR_{23}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_3$, $R_4$, $R_9$, $R_{10}$, $R_{12}$ and $R_{13}$ are each independently H or an optionally substituted $C_1$–$C_6$alkyl group;

$R_5$ is an optionally substituted $C_1$–$C_6$alkyl, aryl or heteroaryl group;

$m$ is 0 or an integer of 1 or 2;

$R_6$ is H, halogen, or an optionally substituted $C_1$–$C_6$alkyl, $C_1$–$C_6$alkoxy, aryl or heteroaryl group;

$R_8$ and $R_{11}$ are each independently H, $CNR_{26}NR_{27}R_{28}$ or a $C_1$–$C_6$alkyl, $C_3$–$C_6$cycloalkyl, cycloheteralkyl, aryl or heteroaryl group each optionally substituted;

$R_{14}$, $R_{15}$, $R_{22}$ and $R_{23}$ are each independently H or an optionally substituted $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group;

$R_{16}$, $R_{17}$, $R_{18}$, $R_{20}$, $R_{20}$, $R_{26}$, $R_{27}$, $R_{28}$, $R_{29}$ and $R_{30}$ are each independently H or $C_1$–$C_4$alkyl;

$R_{19}$ is an optionally substituted $C_1$–$C_6$alkyl, aryl or heteroaryl group;

$R_{24}$ and $R_{25}$ are each independently H or an optionally substituted $C_1$–$C_6$alkyl, aryl or heteroaryl group; and ---- represents a single bond or a double bond; or the stereoisomers thereof or the pharmaceutically acceptable salts thereof.

The present invention further provides methods and compositions useful for the treatment of central nervous system disorders affected by or related to the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. At present, there are no known fully selective agonists. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders.

Surprisingly, it has now been found that heterocyclylindazole or -azaindazole compounds of formula I demonstrate affinity for the 5-HT6 receptor along with significant receptor sub-type selectivity. Advantageously, said formula I compounds are effective therapeutic agents for the treatment of central nervous system (CNS) disorders associated with or affected by the 5-HT6 receptor. Accordingly, the present invention provides heterocyclylindazole or -azaindazole compounds of formula I

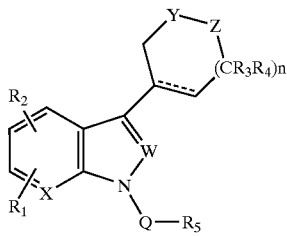

(I)

wherein

Q is $SO_2$, CO, $CONR_{24}$, $CSNR_{25}$ or $CH_2$;

W is N or $CR_6$;

X is N or $CR_7$;

Y is $NR_8$ or $CR_9R_{10}$;

n is 0 or an integer of 1 or 2;

Z is $NR_{11}$ or $CR_{12}R_{13}$ with the proviso that when n is 1, Q is $SO_2$, CO or $CH_2$, and W is $CR_6$ then Z must be $CR_{12}R_{13}$ and with the further provisos that when Y is $NR_8$ then Z must be $CR_{12}R_{13}$ and at least one of Y and Z must be $NR_8$ or $NR_{11}$;

$R_1$, $R_2$ and $R_7$ are each independently H, halogen, CN, $OCO_2R_{14}$, $CO_2R_{15}$, $CONR_{29}R_{30}$, $CNR_{16}NR_{17}R_{18}$, $SO_mR_{19}$, $NR_{20}R_{21}$, $OR_{22}$, $COR_{23}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_3$, $R_4$, $R_9$, $R_{10}$, $R_{12}$ and $R_{13}$ are each independently H or an optionally substituted $C_1$–$C_6$alkyl group;

$R_5$ is an optionally substituted $C_1$–$C_6$alkyl, aryl or heteroaryl group;

m is 0 or an integer of 1 or 2;

$R_6$ is H, halogen, or an optionally substituted $C_1$–$C_6$alkyl, $C_1$–$C_6$alkoxy, aryl or heteroaryl group;

$R_8$ and $R_{11}$ are each independently H, $CNR_{26}NR_{27}R_{28}$ or a $C_1$–$C_6$alkyl, $C_3$–$C_6$cycloalkyl, cycloheteralkyl, aryl or heteroaryl group each optionally substituted;

$R_{14}$, $R_{15}$, $R_{22}$ and $R_{23}$ are each independently H or an optionally substituted $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group;

$R_{16}$, $R_{17}$, $R_{18}$, $R_{20}$, $R_{21}$, $R_{26}$, $R_{27}$, $R_{28}$, $R_{29}$, and $R_{30}$ are each independently H or $C_1$–$C_4$alkyl;

$R_{19}$ is an optionally substituted $C_1$–$C_6$alkyl, aryl or heteroaryl group;

$R_{24}$ and $R_{25}$ are each independently H or an optionally substituted $C_1$–$C_6$alkyl, aryl or heteroaryl group; and ---- represents a single bond or a double bond; or the stereoisomers thereof or the pharmaceutically acceptable salts thereof.

As used in the specification and claims, the term halogen designates Br, Cl, I or F; the term aryl designates phenyl or naphthyl; and the term cycloheteroalkyl designates a 5- to 7-membered monocyclic ring system containing 1 or 2 heteroatoms, which may be the same or different, selected from N, O or S and optionally containing one double bond. Exemplary of the cycloheteroalkyl ring systems included in the term as designated herein are the following rings wherein $Y_1$ is NR, O or S and R is H or an optional substituent as described hereinbelow.

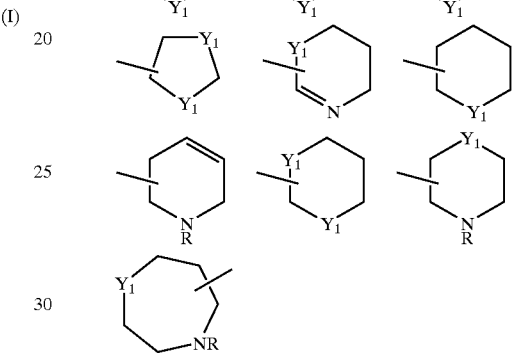

Similarly, as used in the specification and claims, the term heteroaryl designates a 5- to 10-membered monocyclic or bicyclic aromatic ring system containing 1 to 3 heteroatoms, which may be the same or different, selected from N, O or S. Such heteroaryl ring systems include pyrrolyl, azolyl, oxazolyl, thiazolyl, imidazolyl, furyl, thienyl, quinolinyl, isoquinolinyl, indolinyl, benzothienyl, benzofuranyl, benzisoxazolyl and the like. The term haloalkyl designates a $C_nH_{2n+1}$ group having from one to 2n+1 halogen atoms which may be the same or different; and the term haloalkoxy designates an $OC_nH_{2n+1}$ group having from one to 2n+1 halogen atoms which may be the same or different.

In the specification and claims, when the terms $C_1$–$C_6$alkyl, $C_2$–$C_6$alkenyl, $C_2$–$C_6$alkynl, $C_3$–$C_7$cycloalkyl, cycloheteroalkyl, $C_1$–$C_6$alkanoyl, aryl or heteroaryl are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, cycloheteroalkyl, heteroaryl or cycloalkyl groups, preferably halogen atoms or lower alkyl groups. Typically, up to 3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, mandelic, malonic, succinic, fumaric, acetic, lactic, nitric, sulfonic, p-toluene sulfonic, methane sulfonic acid or the like.

Compounds of the invention include esters, carbamates or other conventional prodrug forms, which in general, are functional derivatives of the compounds of the invention and which are readily converted to the inventive active moiety in vivo. Correspondingly, the method of the invention embraces the treatment of the various conditions described hereinabove with a compound of formula I or with a compound which is not specifically disclosed but which, upon administration, converts to a compound of formula I in vivo. Also included are metabolites of the compounds of the present invention defined as active species produced upon introduction of these compounds into a biological system.

Compounds of the invention may exist as one or more stereoisomers. The various stereoisomers include enantiomers, diastereomers, atropisomers and geometric isomers. One skilled in the art will appreciate that one stereoisomer may be more active or may exhibit beneficial effects when enriched relative to the other stereoisomer(s) or when separated from the other stereoisomer(s). Additionally, the skilled artisan knows how to separate, enrich or selectively prepare said stereoisomers. Accordingly, the present invention comprises compounds of Formula I, the stereoisomers thereof and the pharmaceutically acceptable salts thereof. The compounds of the invention may be present as a mixture of stereoisomers, individual stereoisomers, or as an optically active form.

Preferred compounds of the invention are those compounds of formula I wherein n is 1 and Y is $NR_8$. Also preferred are those compounds of formula I wherein n is 0. Further preferred compounds of the invention are those compounds of formula I wherein Q is $SO_2$ or CO and $R_5$ is an optionally substituted aryl or heteroaryl group. Another group of preferred compounds is those compounds of formula I wherein ---- represents a single bond.

More preferred compounds of the invention are those compounds of formula I wherein n is 0; Q is $SO_2$; X is $CR_7$; and Z is $NR_{11}$. Another group of more preferred inventive compounds are those formula I compounds wherein n is 1; Q is $SO_2$; Y is $NR_8$; X is $CR_7$; and $R_5$ is an optionally substituted aryl group. Further more preferred compounds of the invention are those compounds of formula I wherein n is 0; Q is $So_2$; W is $CR_6$; X is $CR_7$; Z is $NR_{11}$; $R_5$ is an optionally substituted aryl group; and ---- represents a single bond.

Among the preferred compounds of the invention are:
1-(phenylsulfonyl)-3-(piperidin-4-yl)-1H-indazole;
1-(4-nitrophenyl)-3-(piperidin-4-yl)-1H-indazole;
1-(4-fluorophenyl)-3-(piperidin-4-yl)-1H-indazole;
1-(3,4-dimethoxyphenyl-3-(piperidin-4-yl)-1H-indazole;
1-(4-fluorophenylsulfonyl)-3-(1-methyl-pyrrolidin-3-yl)-1H-indole;
1-(4-chlorophenylsulfonyl)-3-(1-methylpyrrolidin-3-yl)-1H-indole;
1-(naphth-2-ylsulfonyl)-3-(1-methylpyrrolidin-3-yl)-1H-indole;
1-(4-aminophenylsulfonyl)-3-(1-methylpyrrolidin-3-yl)-1H-indole;
1-(3,4-dimethoxyphenylsulfonyl)-3-(1-methylpyrrolidin-3-yl)-1H-indole;
1-(3,4-dichlorophenylsulfonyl)-3-(1-methylpyrrolidin-3-yl)-1H-indole;
1-[(4,5-dichlorothien-2-yl)sulfonyl]-3-(1-methylpyrrolidin-3-yl)-1H-indole;
1-(2-bromophenylsulfonyl)-3-(1-methylpyrrolidin-3-yl)-1H-indole;
1-(4-iodophenylsulfonyl)-3-(1-methylpyrrolidin-3-yl)-1H-indole;
1-(2-iodophenylsulfonyl)-3-(1-methylpyrrolidin-3-yl)-1H-indole;
1-(4-aminophenylsulfonyl)-3-(1-benzylpyrrolidin-3-yl)-1H-indole;
3-(1-benzylpyrrolidin-3-yl)-1-(4-methylphenylsulfonyl)-1H-indole;
3-(1-benzylpyrrolidin-3-yl)-1-(3,4-dichlorophenyl-sulfonyl)-1H-indole;
3-(1-benzylpyrrolidin-3-yl)-1-(2-bromophenylsulfonyl)-1H-indole;
5-[3-(1-benzylpyrrolidin-3-yl)-indole-1-sulfonyl]-4-methyl-thiazol-2-ylamine;
3-(1-benzylpyrrolidin-3-yl)-1-[(5-bromothien-2-yl)sulfonyl]-1H-indole;
1-phenylsulfonyl-3-(1-methylpyrrolidin-3-yl)-1H-pyrrolo[2,3-b]pyridine;
1-phenylsulfonyl-3-(1-methylpyrrolidin-3-yl)-1H-indazole;
1-phenylsulfonyl-3-(1-methyl-2,5-dihydro-1H-pyrrol-3-yl)-1H-pyrrolo[2,3-b]pyridine;
1-phenylsulfonyl-3-(1-methyl-2,5-dihydro-1H-pyrrol-3-yl)-1H-indole;
1-phenylsulfonyl-3-(1-methylpiperidin-4-yl)-1H-indazole;
1-phenylsulfonyl-3-(1-methyl-1,2,3,6-tetrahydropyridin-4-yl)-1H-indazole;
1-phenylsulfonyl-3-(1-methylazepan-4-yl)-1H-pyrrolo[2,3-b]pyridine;
1-phenylsulfonyl-3-(1-methylazepan-4-yl)-1H-indole;
1-phenylsulfonyl-5-fluoro-3-(1-methylazepan-4-yl)-1H-indole;
1-phenylsulfonyl-3-(1-methyl-2,3,6,7-tetrahydro-1H-azepin-4-yl)-1H-indole;
1-phenylsulfonyl-3-(1-methyl-2,5,6,7-tetrahydro-1H-azepin-4-yl)-1H-indole;
1-phenylsulfonyl-3-(1-methyl-2,3,6,7-tetrahydro-1H-azepin-4-yl)-1H-pyrrolo[2,3-b]pyridine;
1-phenylsulfonyl-5-fluoro-3-(1-methyl-2,3,6,7-tetrahydro-1H-azepin-4-yl)-1H-indole;
1-phenylsulfonyl-5-fluoro-3-(1-methyl-2,5,6,7-tetrahydro-1H-azepin-4-yl)-1H-indole;
1-(benzo[b]thioen-4-ylsulfonyl)-3-(1-methyl-pyrrolidin-3-yl)-1H-pyrrolo[2,3-b]pyridine;
1-(3-fluorophenylsulfonyl)-3-(1-methylpyrrolidin-3-yl)-1H-indazole;
1-(2,5-dichlorophenylsulfonyl)-3-(2,5-dihydro-1H-pyrrol-3-yl)-1H-pyrrolo[2,3-b]pyridine;
8-[3-(1-methyl-2,5-dihydro-1H-pyrrol-3-yl)indole-1-sulfonyl]-quinoline;
1-phenylsulfonyl-5-chloro-3-(1-methylpiperidin-4-yl)-1H-indazole;
5-methoxy-3-(1-methyl-1,2,3,6-tetrahydropyridin-4-yl)-1-(naphth-1-yl-sulfonyl)-1H-indazole;
3-(1-methylazepan-4-yl)-1-(naphth-1-yl-sulfonyl)-1H-pyrrolo[2,3-b]pyridine;
3-(1-methylazepan-4-yl)-1-(naphth-1-yl-sulfonyl)-1H-indole;
1-(benzo[b]thien-4-ylsulfonyl)-5-fluoro-3-(1-methylazepan-4-yl)-1H-indole;
8-[3-(1-methyl-2,3,6,7-tetrahydro-1H-azepin-4-yl)-indole-1-sulfonyl]-quinoline;
3-(1-methyl-2,5,6,7-tetrahydro-1H-azepin-4-yl)-1-(naphth-1-ylsulfonyl)-1H-indole;
8-[3-(1-methyl-2,3,6,7-tetrahydro-1H-azepin-4-yl)-pyrrolo[2,3-b]pyridine-1-sulfonyl]-quinoline;

8-[5-fluoro-3-(1-methyl-2,3,6,7-tetrahydro-1H-azepin-4-yl)-indole-1-sulfonyl]-quinoline;
5-fluoro-3-(1-methyl-2,5,6,7-tetrahydro-1H-azepin-4-yl)-1-(naphth-1-ylsulfonyl)-1H-indole;
1-(benzo[b]thien-4-ylsulfonyl)-3-(1-benzyl-pyrrolidin-3-yl)-1H-pyrrolo[2,3-b]pyridine;
1-(3-fluoro-phenylsulfonyl)-3-(1-phenethyl-pyrrolidin-3-yl)-1H-indazole;
1-(2,5-dichlorophenylsulfonyl)-3-(1-ethyl-2,5-dihydro-1H-pyrrol-3-yl)-1H-pyrrolo[2,3-b]pyridine;
3-(1-methyl-2,5-dihydro-1H-pyrrol-3-yl)-1-(naphth-2-ylsulfonyl)-1H-indole;
5-chloro-1-(3-fluorophenylsulfonyl)-3-piperidin-4-yl-1H-indazole;
5-methoxy-1-(naphth-1-ylsulfonyl)-3-(1,2,2-trimethyl-1,2,3,6-tetrahydro-pyridin-4-yl)-1H-indazole;
1-(naphth-1-ylsulfonyl)-3-(1-phenethyl-azepan-4-yl)-1H-pyrrolo[2,3-b]pyridine;
3-azepan-4-yl-1-(naphth-1-ylsulfonyl)-1H-indole;
3-azepan-4-yl-1-(3-chloro-5-methyl-benzo[b]thien-2-ylsulfonyl)-5-fluoro-1H-indole;
8-[3-(1-phenethyl-2,3,6,7-tetrahydro-1H-azepin-4-yl)-indole-1-sulfonyl]-quinoline;
3-[1-(3,3-dimethylbutyl)-2,5,6,7-tetrahydro-1H-azepin-4-yl]-1-(naphth-2-ylsulfonyl)-1H-indole;
1-(2,3-dichlorophenylsulfonyl)-3-(1-methyl-2,3,6,7-tetrahydro-1H-azepin-4-yl)-1H-pyrrolo[2,3-]pyridine;
1-[(3-chloro-5-methoxyphenylsulfonyl)]-3-(2,2-dimethyl-2,3,6,7-tetrahydro-1H-azepin-4-yl)-5-fluoro-1H-indole;
3-azepan-4-yl-5-fluoro-1-(naphth-2-ylsulfonyl)-1H-indole;
1-benzenesulfonyl-3-piperidin-3-yl-1H-indole;
1-(4-isopropyl-benzenesulfonyl)-3-piperidin-3-yl-1H-indole;
1-(5-chloro-thiophene-2-sulfonyl)-3-piperidin-3-yl-1H-indole;
1-(3-chloro-benzenesulfonyl)-3-piperidin-3-yl-1H-indole;
1-(3,4-difluoro-benzenesulfonyl)-3-piperidin-3-yl-1H-indole;
1-(4-trifluoromethoxy-benzenesulfonyl)-3-piperidin-3-yl-1H-indole;
1-(4-methoxy-benzenesulfonyl)-3-piperidin-3-yl-1H-indole;
1-(4-trifluoromethy-benzenesulfonyl)-3-piperidin-3-yl-1H-indole;
1-(3-chloro-4-methyl-benzenesulfonyl)-3-piperidin-3-yl-1H-indole;
1-(2-chloro-4-trifluoromethyl-benzenesulfonyl)-3-piperidin-3-yl-1H-indole;
1-(2-naphthylenesulfonyl)-3-piperidin-3-yl-1H-indole;
1-(5-chloro-3-methyl-benzo[b]thiophene-2-sulfonyl)-3-piperidin-3-yl-1H-indole;
1-(2,6-dichloro-imidazo[2,1-b]thiazole-5-sulfonyl)-3-piperidin-3-yl-1H-indole;
2-chloro-3-(3-piperidin-3-yl-indole-1-sulfonyl)-imidazo[1,2-a]pyridine;
2-chloro-3-(3-piperidin-3-yl-indole-1-sulfonyl)-benzo[d]imidazo[2,1-b]thiazole;
1-(4-isopropyl-benzenesulfonyl)-3-piperidin-3-yl-1H-pyrrolo[2,3-b]pyridine;
1-(5-chloro-thiophene-2-sulfonyl)-3-piperidin-3-yl-1H-pyrrolo[2,3-b]pyridine;
1-(3-chloro-benzenesulfonyl)-3-piperidin-3-yl-1H-pyrrolo[2,3-b]pyridine;
1-(3,4-difluoro-benzenesulfonyl)-3-piperidin-3-yl-1H-pyrrolo[2,3-b]pyridine;
1-(4-trifluoromethoxy-benzenesulfonyl)-3-piperidin-3-yl-1H-pyrrolo[2,3-b]pyridine;
1-(3-chloro-4-methyl-benzenesulfonyl)-3-piperidin-3-yl-1H-pyrrolo[2,3-b]pyridine;
1-(2-chloro-4-trifluoromethyl-benzenesulfonyl)-3-piperidin-3-yl-1H-pyrrolo[2,3-b]pyridine;
1-(2-naphthylenesulfonyl)-3- piperidin-3-yl-1H-pyrrolo[2,3-b]pyridine;
1-(5-chloro-3-methyl-benzo[b]thiophene-2-sulfonyl)-3-piperidin-3-yl-1H-pyrrolo[2,3-b]pyridine;
2-chloro-3-(3-piperidin-3-yl-pyrrolo[2,3-b]pyridine-1-sulfonyl)-imidazo[1,2-a]pyridine;
2-chloro-3-(3-piperidin-3-yl-pyrrolo[2,3-b]pyridine-1-sulfonyl)-benzo[d]imidazo[2,1-b]thiazole;

or the pharmaceutically acceptable salts thereof.

Compounds of the invention may be prepared using conventional synthetic methods and, if required, standard separation or isolation techniques. For example, compounds of formula I wherein n is 1; Q is SO$_2$; Y is CH$_2$; Z is NH; and ---- represents a double bond (Ia) may be prepared by reacting a compound of formula II with a protected 4-piperidone compound of formula III, such as 1-t-butoxycarbonyl-4-piperidone, in the presence of a base to give the protected tetrahydropyridinyl compound of formula IV; sulfonating said formula IV compound to give the protected 1-sulfonyl derivative of formula V; and deprotecting the formula V compound to give the desired formula Ia product. Alternatively, the formula V compound may be reduced to give the formula VI protected piperidin-4-yl derivative and deprotection of the formula VI compound affords the compound of formula I wherein n is 1; Q is SO$_2$; Y is CH$_2$, Z is NH; and ---- represents a single bond (1b). The reaction schemes are shown in flow diagram I wherein G represents a protecting group.

FLOW DIAGRAM I

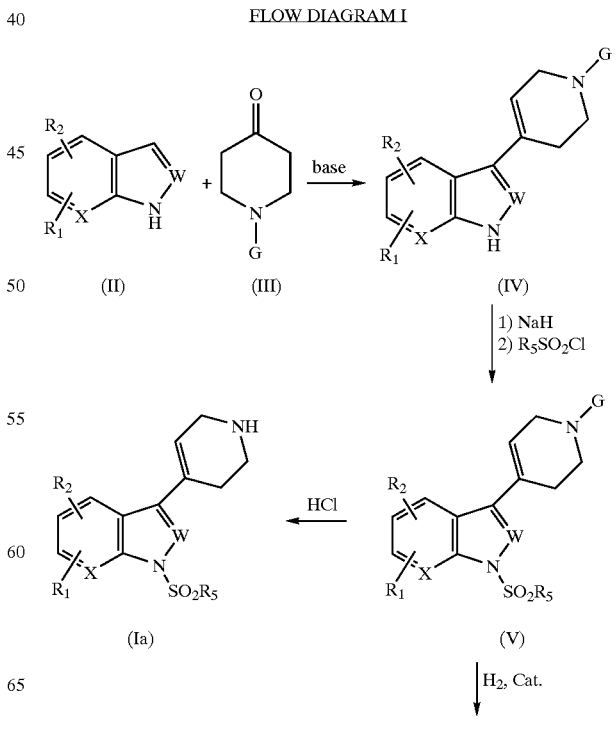

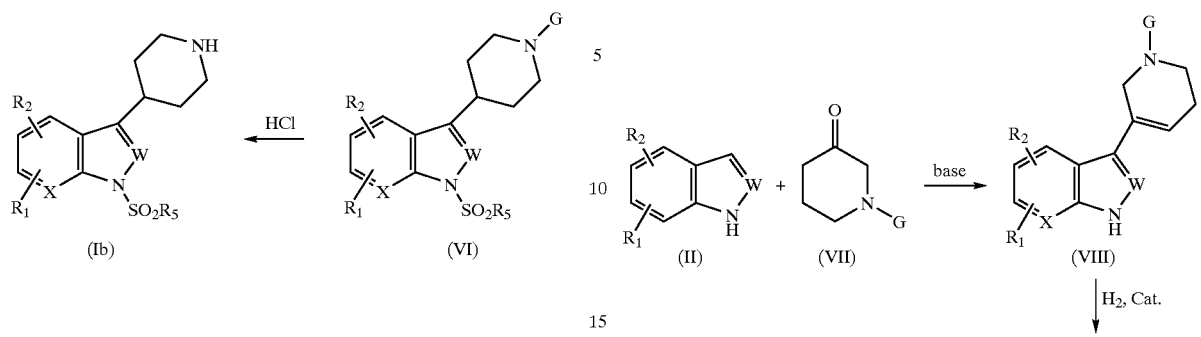

Commonly used protecting groups include t-butylcarboxylate, benzyl, acetyl, benzyloxycarbonyl, or any conventional group known to protect a basic nitrogen in standard synthetic procedures.

The corresponding compounds of formula I wherein Z is $NR_{11}$ and $R_{11}$ is other than H may be prepared by alkylating the formula Ia or Ib compound with an alkylating agent $R_{11}$-Hal, wherein Hal is Cl, Br or I. The reaction is illustrated in flow diagram II.

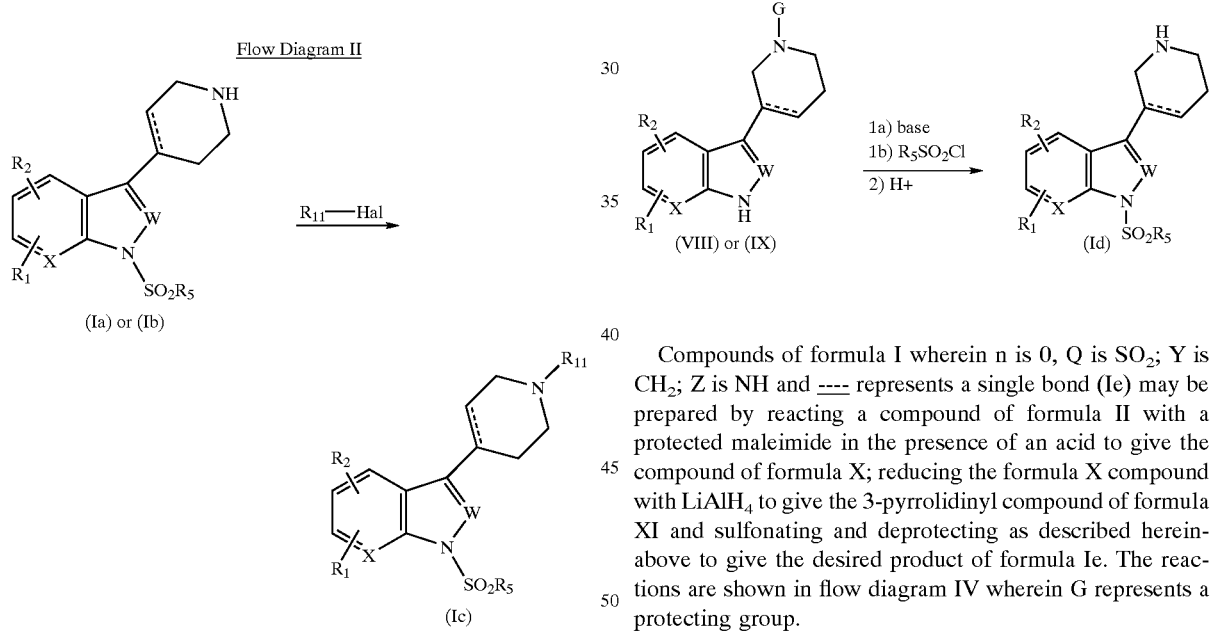

Similarly, compounds of formula I wherein n is 1; Q is $SO_2$; Y is NH and Z is $CH_2$ (Id) may be prepared by reacting a formula II compound with a protected 3-piperidone of formula VII in the presence of a base to give the protected tetrahydropyridinyl compound of formula VIII; reducing said formula VIII compound via catalytic hydrogenation to give the compound of formula IX; sulfonating the formula VIII or IX compound to give the corresponding protected 1-sulfonyl derivative and deprotecting said derivative to give the desired product of formula Id. The reaction sequence is shown in flow diagram III wherein G represents a protecting group.

Compounds of formula I wherein n is 0, Q is $SO_2$; Y is $CH_2$; Z is NH and ---- represents a single bond (Ie) may be prepared by reacting a compound of formula II with a protected maleimide in the presence of an acid to give the compound of formula X; reducing the formula X compound with $LiAlH_4$ to give the 3-pyrrolidinyl compound of formula XI and sulfonating and deprotecting as described hereinabove to give the desired product of formula Ie. The reactions are shown in flow diagram IV wherein G represents a protecting group.

FLOW DIAGRAM IV

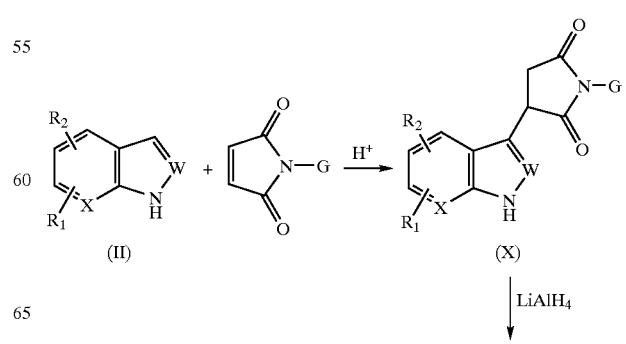

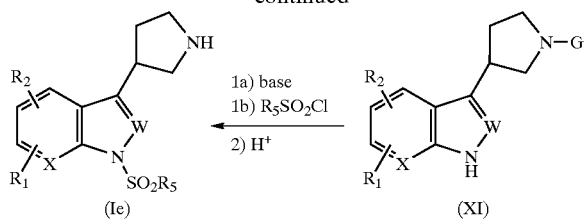

Utilizing the reactions shown in flow diagrams I, II, and III hereinabove and employing the appropriate pyrrolidone or homopiperidone affords compounds of formula I wherein n is 0 or 2 and Q is $SO_2$. Compounds of formula Id or Ie may be alkylated as shown in flow diagram III to give the corresponding formula I products wherein $R_8$ or $R_{11}$ is other than H. Compounds of formula I wherein Q is CO, $CONR_{24}$ or $CH_2$ may be prepared by reacting the protected intermediate of formula IV, VIII, IX or XI with the appropriate carbonyl halide, carbamoyl halide or alkyl halide, respectively. These and other literature procedures may be utilized to prepare the formula I compounds of the invention.

Advantageously, the inventive compound of formula I may be utilized in the treatment of central nervous system disorders relating to or affected by the 5-HT6 receptor such as motor, mood, psychiatric, cognitive, neurodegenerative, or the like disorders. In particular, CNS disorders such as anxiety, depression, schizophrenia, Alzheimer's disease, Parkinson's disease, eating disorders, disorders related to alcohol or drug withdrawl, sexual dysfunction, attention deficit, memory loss or the like. Accordingly, the present invention provides a method for the treatment of a disorder of the central nervous system (CNS) related to or affected by the 5-HT6 receptor in a patient in need thereof which comprises providing said patient with a therapeutically effective amount of a compound of formula I as described hereinabove. The compounds may be provided via oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are administered in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired.

Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms HPLC and NMR designate high performance liquid chromatography and nuclear magnetic resonance, respectively.

EXAMPLE 1

Preparation of 3-(1H-Indol-3-yl)-1-methylpyrrolidine-2,5-dione

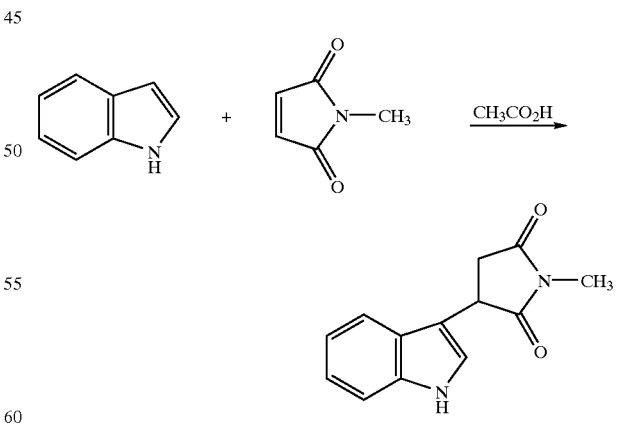

A mixture of indole (3.14 g) and N-methylmaleimide (6.2 g, 3 equiv.) in acetic acid is heated at 105° C. for 16 hr, cooled to room temperature, held for 16 hr and filtered. The filtercake is washed with acetic acid and dried to afford the title product, 5.5 g, identified by HPLC and mass spectral analyses.

EXAMPLE 2

Preparation of 3-(1-methylpyrrolidin-3-yl)-1H-indole

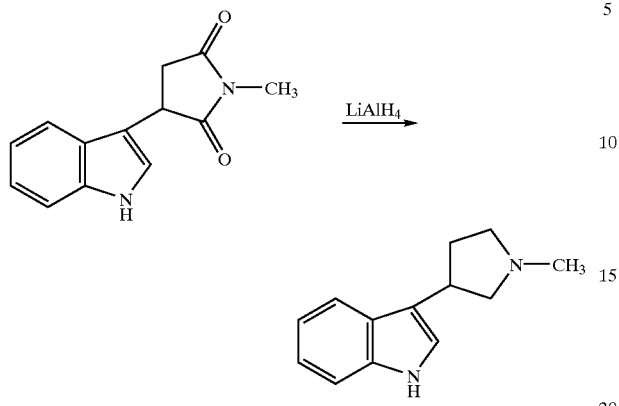

A solution of 3-(1-H-indol-3-yl)-1-methyl-pyrrolidine-2,5-dione (1.4 g) in tetrahydrofuran is treated with LiAlH$_4$ (12 mL, 1.0 M solution, 2 equiv), stirred at 50° C. for 8 hr, cooled to room temperature, quenched with water and 15% aqueous NaOH and filtered. The filtrate is dried over MgSO$_4$ and concentrated in vacuo to afford the title product as an oil, 1.1 g, identified by HPLC and mass spectral analyses.

EXAMPLE 3

Preparation of 3-(1-methylpyrrolidin-3-yl)-1-[4-(methylphenyl)sulfonyl]-1H-indole

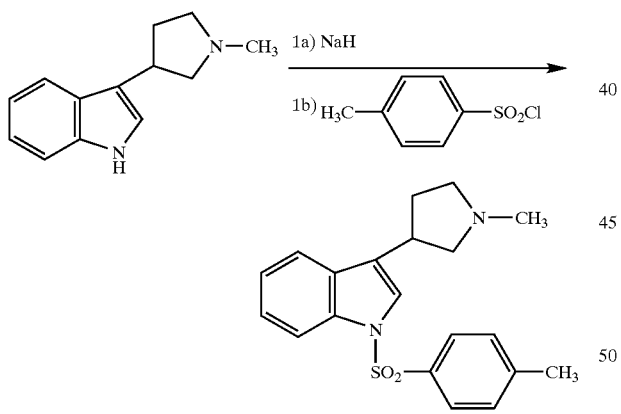

A solution of 3-(1-methylpyrrolidin-3-yl)-1H-indole (50.1 mg, 0.25 mmol) in tetrahydrofuran is treated sequentially with NaH (60% dispersion in mineral oil, 0.75 mmol) and 4-methylphenylsulfonyl chloride (47 mg, 0.25 mmmol), stirred for 12 hr and concentrated in vacuo to give a residue. Purification of the residue by HPLC affords the title product as a solid, characterized by HPLC and mass spectral analyses, [M+H] 355.15, LCMS[1] retention time 1.82 min.

[1]LCMS conditions: HP1100 MSD system; Waters Xterra C18, 2 mm×50 mm ID, 5 uM column; 10 uL injectin; Solvent A: 0.02% TFA/water; Solvent B:0.02% TFA/acetonitrile; Gradient: Time 0: 95% A; 0.3 min: 95% A; 5 min: 10% A, Flow rate 1 mL/min; Detection: 254 nm DAD.

EXAMPLES 4–27

Preparation of 1-(Arylsulfonyl)-3-(N-substituted-pyrrolidin-3-yl)-1H-Indole

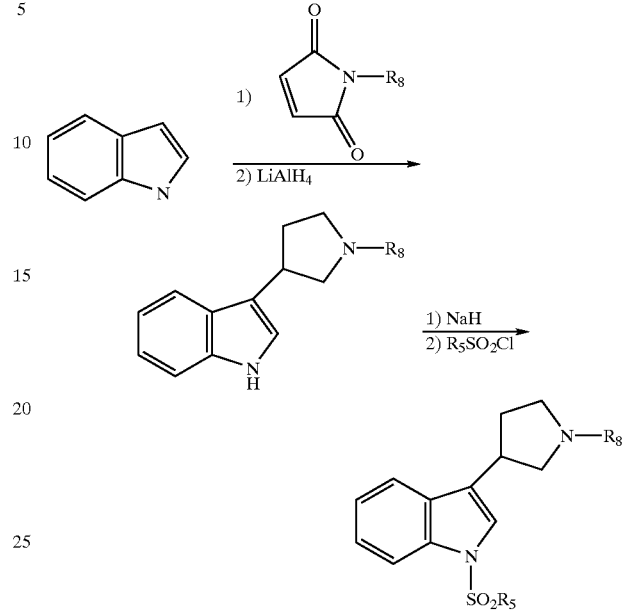

Using essentially the same procedures described in Examples 3, 4 and 5 and employing the appropriate maleimide and suitable arylsulfonyl chloride the compounds shown in Table II are prepared and identified by HPLC and mass spectral analyses. (LCMS[1])

[1]LCMS conditions: HP1100 MSD system; Waters Xterra C18, 2 mm×50 mm ID, 5 uM column; 10 uL injectin; Solvent A: 0.02% TFA/water; Solvent B:0.02% TFA/acetonitrile; Gradient: Time 0: 95% A; 0.3 min: 95% A; 5 min: 10% A, Flow rate 1 mL/min; Detection: 254 nm DAD.

TABLE II

| Ex. No. | R$_8$ | R5 | M + H | LCMS (min) |
|---|---|---|---|---|
| 4 | methyl | 4-fluorophenyl | 359 | 1.78 |
| 5 | methyl | 4-methoxyphenyl | 371 | 1.82 |
| 6 | methyl | 4-chlorophenyl | 375 | 1.90 |
| 7 | methyl | 5-chlorothien-2-yl | 381 | 1.94 |
| 8 | methyl | 2-naphthyl | 391 | 2.05 |
| 9 | methyl | 4-anilinyl | 356 | 1.58 |
| 10 | methyl | 3,4-dimethoxyphenyl | 401 | 1.74 |
| 11 | methyl | 3,4-dichlorophenyl | 409 | 2.07 |
| 12 | methyl | 4,5-dichlorothien-2-yl | 415 | 2.14 |
| 13 | methyl | 2-bromophenyl | 419 | 1.84 |
| 14 | methyl | 2-amino-4-methylthiazol-5-yl | 377 | 1.53 |
| 15 | methyl | 5-chloro-3-methyl-1-benzothien-2-yl | 445 | 2.28 |
| 16 | methyl | 4-iodophenyl | 467 | 1.88 |
| 17 | methyl | 2-iodophenyl | 467 | 2.00 |
| 18 | benzyl | 4-methylphenyl | 431 | 2.17 |
| 19 | benzyl | 4-methoxyphenyl | 447 | 2.14 |
| 20 | benzyl | 4-aminophenyl | 432 | 1.68 |
| 21 | benzyl | 3,4-dichlorophenyl | 487 | 2.40 |

TABLE II-continued

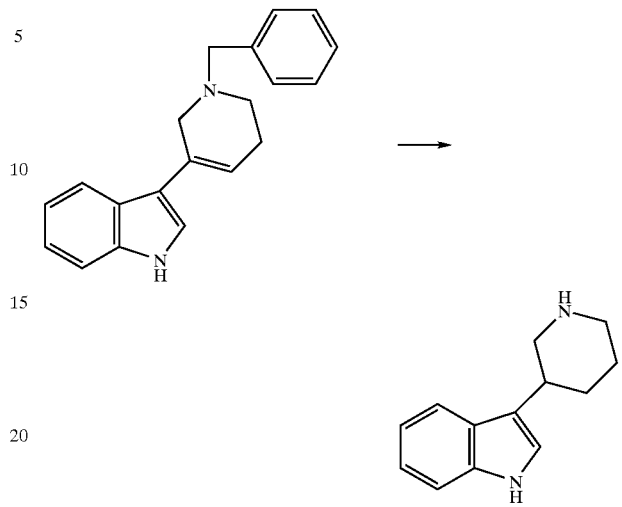

| Ex. No. | R8 | R5 | M + H | LCMS (min) |
|---|---|---|---|---|
| 22 | benzyl | 2-bromophenyl | 495 | 2.15 |
| 23 | benzyl | 2-amino-4-methylthiazol-5-yl | 453 | 1.60 |
| 24 | benzyl | 5-bromothien-2-yl | 501 | 2.30 |
| 26 | benzyl | 4-iodophenyl | 543 | 2.21 |
| 27 | benzyl | 2-iodophenyl | 543 | 2.34 |

EXAMPLE 28

Preparation of 3-(1-Benzyl-1,2,5,6-tetrahydro-pyridin-3-yl)-1H-indole

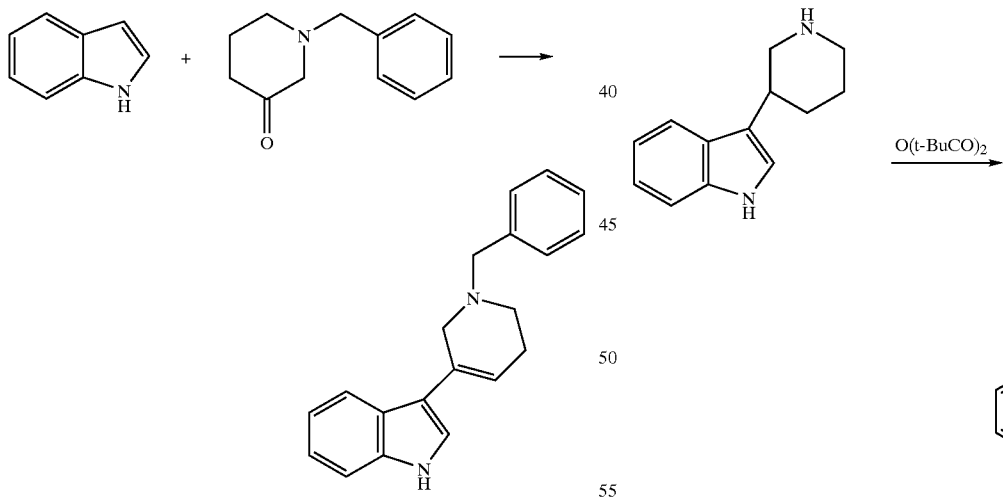

A mixture of indole (29, 17 mmol) and 1-benzyl-piperidin-3-one hydrochloride hydrate (7.7 g, 34 mmol) and 2N KOH/isopropanol is heated at 80° C. for 14 hours, cooled to room temperature, poured over ice/water and extracted with ethyl acetate. The extracts are combined, washed with water, dried over $Na_2SO_4$ and concentrated in vacuo to afford the title product, identified by HPLC and mass spectral analyses.

EXAMPLE 29

Preparation of 3-Piperidin-3-yl-1H-indole

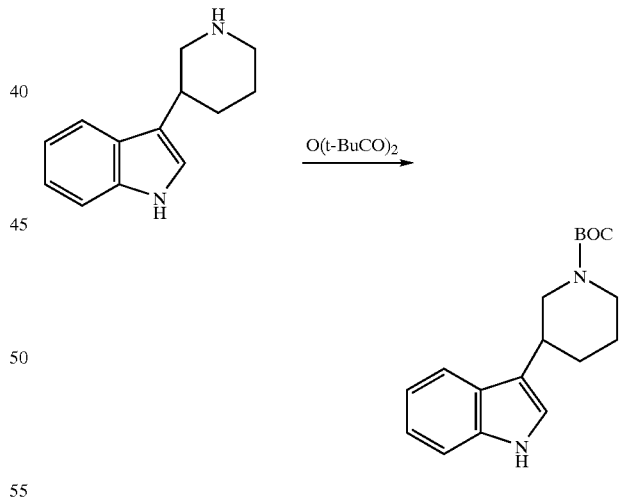

A mixture of the 3-(1-benzyl-1,2,5,6-tetrahydro-pyridin-3-yl)-1H-indole obtained in Example 28 and 10% palladium on carbon in a mixture of formic acid and methanol is stirred at room temperature for 3 days and filtered through celite. The celite is washed with methanol. The filtrates are combined and concentrated in vacuo to afford the title product, identified by HPLC and mass spectral analyses.

EXAMPLE 30

Preparation of 3-(1H-Indol-3-yl)-piperidine-1–carboxylic acid tert-butyl ester

A solution of the 3-piperidin-3-yl-1H-indole obtained in Example 29 in acetone/water (1:1) at 0° C. is treated with di-tert-dicarbonate (4.1 g, 18.7 mmol) and $K_2CO_3$ (11.75 g, 85 mmol), stirred for 2 hours while warming to room temperature, and concentrated in vacuo. The resultant aqueous mixture is extracted with ethyl acetate. The extracts are combined, dried over $Na_2SO_4$ and concentrated in vacuo. The resultant residue is purified by column chromatography (silica gel, 1% $NH_4OH$ in $MeOH:CHCl_3$, 0:100 to 10:90 as eluent) to afford the title product, 1.25 g, identified by HPLC and mass spectral analyses.

EXAMPLE 31

Preparation of 1-Benzenesulfonyl-3-piperidin-3-yl-1H-indole

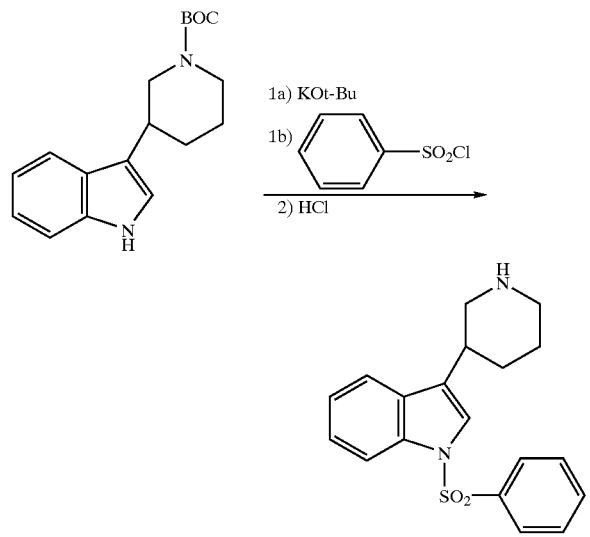

A solution of 3-(1H-indol-3-yl)-piperidine-1–carboxylic acid tert-butyl ester (75 mg, 0.25 mmol) and phenylsulfonyl chloride (50 mg, 0.27 mmol) in tetrahydrofuran (THF) at room temperature is treated with potassium tert-butoxide (0.275 mL, 1 M solution in THF, 0.275 mmol), shaken at room temperature for 16 hours, treated with HCl (4 N in dioxane, 0.5 mL), shaken for 2 hours and concentrated in vacuo to give a residue. Purification of the residue by HPLC[1] affords the title product, characterized by HPLC and mass spectral analyses [M+H] 341.45, LCMS[2] retention time 1.67 min.

[1]HPLC conditions: Gilson Preparative HPLC system; YMC Pro C18, 20 mm×50 mm ID, 5uM column; 2 mL injection; Solvent A: 0.02% TFA/water; Solvent B:0.02% TFA/acetonitrile; Gradient: Time 0: 95% A; 2 min: 95% A; 14 min: 10% A, 15 min: 10% A, 16 min: 95% A; Flow rate 22.5 mL/min; Detection: 254 nm DAD.
[2]LCMS conditions: HP1100 MSD system; Waters Xterra C18, 2 mm×50 mm ID, 5 uM column; 10 uL injectin; Solvent A: 0.02% TFA/water; Solvent B:0.02% TFA/acetonitrile; Gradient: Time 0: 95% A; 0.3 min: 95% A; 5 min: 10% A, Flow rate 1 mL/min; Detection: 254 nm DAD.

EXAMPLES 32–57

Preparation of 1-Arylsulfonyl-3-piperidin-3-yl-1H-indole

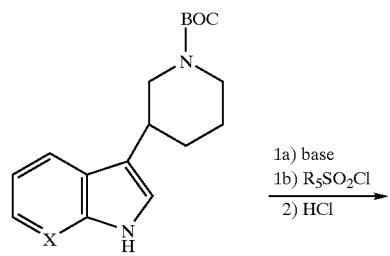

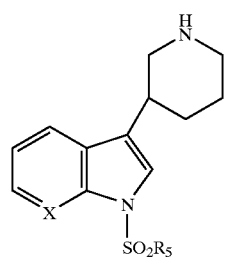

Using essentially the same procedures described in Examples 28–31 and employing the appropriate indole or azaindole substrate and a suitable arylsulfonyl chloride the compounds shown in Table III are prepared and identified by HPLC and mass spectral analyses. (LCMS[1])

[1]LCMS conditions: HP1100 MSD system; Waters Xterra C18, 2 mm×50 mm ID, 5 uM column; 10 uL injectin; Solvent A: 0.02% TFA/water; Solvent B:0.02% TFA/acetonitrile; Gradient: Time 0: 95% A; 0.3 min: 95% A; 3 min: 10% A, Flow rate 1 mL/min; Detection: 254 nm DAD.

TABLE III

| Ex. No. | R5 | X | M + H | LCMS (min) |
|---|---|---|---|---|
| 32 | 4-isopropylphenyl | CH | 384 | 1.95 |
| 33 | 5-chlorothien-2-yl | CH | 382 | 1.83 |
| 34 | 3-chlorophenyl | CH | 376 | 1.90 |
| 35 | 3,4-difluorophenyl | CH | 377 | 1.79 |
| 36 | 4-trifluoromethoxyphenyl | CH | 425 | 1.94 |
| 37 | 4-methoxyphenyl | CH | 371 | 1.76 |
| 38 | 4-trifluoromethylphenyl | CH | 409 | 1.94 |
| 39 | 3-chloro-4-methylphenyl | CH | 390 | 1.96 |
| 40 | 2-chloro-4-trifluorophenyl | CH | 444 | 2.02 |
| 41 | 2-naphthyl | CH | 392 | 1.94 |
| 42 | 5-chloro-3-methylbenzo[B]-thiene-2-yl | CH | 446 | 2.15 |
| 43 | 2,6-dichloro-imidazo[2,1-b]thiazol-5-yl | CH | 456 | 1.90 |
| 44 | 2-Chloro-imidazo[1,2-a]pyrid-3-yl | CH | 416 | 1.72 |
| 45 | 2-Chloro-benzo[d]imidazo-[2,1-b]thia-zol-3-yl | CH | 472 | 1.92 |
| 46 | 4-isopropylphenyl | N | 385 | 1.95 |
| 47 | 5-chlorothien-2-yl | N | 383 | 1.63 |
| 48 | 3-chlorophenyl | N | 377 | 1.65 |
| 49 | 3,4-difluorophenyl | N | 378 | 1.62 |
| 50 | 4-trifluoromethoxyphenyl | N | 426 | 1.94 |
| 51 | 4-trifluoromethylphenyl | N | 410 | 1.86 |
| 52 | 3-chloro-4-methylphenyl | N | 391 | 1.84 |
| 53 | 2-chloro-4-trifluorophenyl | N | 445 | 1.99 |
| 54 | 2-naphthyl | N | 393 | 1.82 |
| 55 | 2,6-dichloro-imidazo[2,1-b]thiazol-5-yl | N | 447 | 2.13 |
| 56 | 2-Chloro-imidazo[1,2-a]-pyrid-3-yl | N | 417 | 1.63 |
| 57 | 2-Chloro-benzo[d]-imidazo[2,1-b]thia-zol-3-yl | N | 473 | 1.88 |

EXAMPLE 58

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10–25 µl volumes. Bovine Serum Albumin is used as the standard in the protein determination according to the method described in Lowry et al., J. Biol. Chem., 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 µl. To each well is added the following mixture: 80.0 µl of incubation buffer made in 50 mM Tris.HCl buffer (pH 7.4) containing 10.0 mM $MgCl_2$ and 0.5 mM EDTA and 20 µl of [$^3$H]-LSD (S.A., 86.0 Ci/mmol, available from Amersham Life Science), 3.0 nM. The dissociation constant, $K_D$ of the [$^3$H]LSD at the human serotonin 5-HT6receptor is 2.9 nM, as determined by saturation binding with increasing concentrations of [$^3$H] LSD. The reaction is initiated by the final addition of 100.0 µl of tissue suspension. Nonspecific binding is measured in the presence of 10.0 µM methiothepin. The test compounds are added in 20.0 µl volume.

The reaction is allowed to proceed in the dark for 120 min at room temperature, at which time, the bound ligand-receptor complex is filtered off on a 96 well unifilter with a Packard Filtermate® 196Harvester. The bound complex caught on the filter disk is allowed to air dry and the radioactivity is measured in a Packard TopCount® equipped with six photomultiplier detectors, after the addition of 40.0 µl Microscint®-20 scintillant to each shallow well. The unifilter plate is heat-sealed and counted in a PackardTop-Count® with a tritium efficiency of 31.0%.

Specific binding to the 5-HT6 receptor is defined as the total radioactivity bound less the amount bound in the presence of 10.0 µM unlabeled methiothepin. Binding in the presence of varying concentrations of test compound is expressed as a percentage of specific binding in the absence of test compound. The results are plotted as log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table IV, below.

TABLE IV

| Test Compound (Ex. No.) | 5-HT6 Binding Ki (nM) |
|---|---|
| 4 | 2 |
| 6 | 1 |
| 8 | 3 |
| 9 | 1 |
| 10 | 5 |
| 11 | 3 |
| 12 | 4 |
| 13 | 1 |
| 16 | 1 |
| 17 | 2 |
| 18 | 8 |
| 20 | 1 |
| 21 | 15 |
| 22 | 14 |
| 23 | 3 |
| 24 | 9 |
| 31 | 2 |
| 32 | 5 |
| 33 | 3 |
| 34 | 2 |
| 35 | 7 |
| 37 | 10 |
| 38 | 10 |
| 39 | 6 |
| 41 | 8 |
| 47 | 7 |
| 48 | 6 |
| Clozapine | 6.0 |
| Loxapine | 41.4 |
| Methiothepin | 8.3 |
| Bromocriptine | 23.0 |
| Mianserin | 44.2 |
| Olzanzepine | 19.5 |

As can be seen from the data in Table II, the compounds of the invention demonstrate a high affinity for the 5-HT6 receptor.

What is claimed is:

1. A compound of formula I

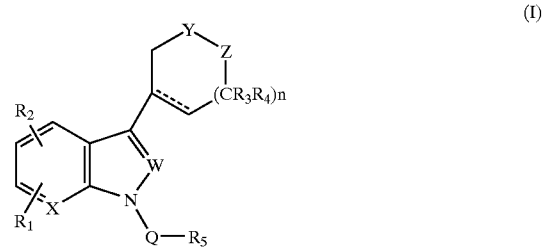

wherein
Q is $SO_2$;
W is N or $CR_6$;
X is N or $CR_7$;
Y is $NR_8$ or $CR_9R_{10}$;
n is 0;
Z is $NR_{11}$ or $CR_{12}R_{13}$ with the proviso that when Y is $NR_8$ then Z must be $CR_{12}R_{13}$ and at least one of Y and Z must be $NR_8$ or $NR_{11}$;
$R_1$, $R_2$ and $R_7$ are each independently H, halogen, CN, $OCO_2R_{14}$, $CO_2R_{15}$, $CONR_{29}R_{30}$, $CNR_{16}NR_{17}R_{18}$, $SO_mR_{19}$, $NR_{20}R_{21}$, $OR_{22}$, $COR_{23}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;
$R_3$, $R_4$, $R_9$, $R_{10}$, $R_{12}$ and $R_{13}$ are each independently H or an optionally substituted $C_1$–$C_6$alkyl group;

$R_5$ is an optionally substituted $C_1$–$C_6$alkyl, aryl or heteroaryl group;

m is 0 or an integer of 1 or 2;

$R_6$ is H, halogen, or an optionally substituted $C_1$–$C_6$alkyl, $C_1$–$C_6$alkoxy, aryl or heteroaryl group;

$R_8$ and $R_{11}$ are each independently H, $CNR_{26}NR_{27}R_{28}$ or a $C_1$–$C_6$alkyl, $C_3$–$C_6$cycloalkyl, cycloheteroalkyl, aryl or heteroaryl group each optionally substituted;

$R_{14}$, $R_{15}$, $R_{22}$ and $R_{23}$ are each independently H or an optionally substituted $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group;

$R_{16}$, $R_{17}$, $R_{18}$, $R_{20}$, $R_{21}$, $R_{26}$, $R_{27}$, $R_{28}$, $R_{29}$ and $R_{30}$ are each independently H or $C_1$–$C_4$alkyl;

$R_{19}$ is an optionally substituted $C_1$–$C_6$alkyl, aryl or heteroaryl group;

$R_{24}$ and $R_{25}$ are each independently H or an optionally substituted $C_1$–$C_6$alkyl, aryl or heteroaryl group; and ---- represents a single bond or a double bond; or the stereoisomers thereof or the pharmaceutically acceptable salts thereof.

2. The compound according to claim 1 wherein Y is $NR_8$.
3. The compound according to claim 1 wherein W is $CR_6$.
4. The compound according to claim 3 wherein Z is $NR_{11}$.
5. The compound according to claim 1 wherein $R_5$ is an optionally substituted aryl or heteroaryl group.
6. The compound according to claim 5 wherein X is CH and ---- represents a single bond.
7. The compound according to claim 1 selected from the group consisting of:

1-(4-fluorophenylsulfonyl)-3-(1-methyl-pyrrolidin-3-yl)-1H-indole;
1-(4-chlorophenylsulfonyl)-3-(1-methylpyrrolidin-3-yl)-1H-indole;
1-(naphth-2-ylsulfonyl)-3-(1-methylpyrrolidin-3-yl)-1H-indole;
1-(4-aminophenylsulfonyl)-3-(1-methylpyrrolidin-3-yl)-1H-indole;
1-(3,4-dimethoxyphenylsulfonyl)-3-(1-methylpyrrolidin-3-yl)-1H-indole;
1-(3,4-dichlorophenylsulfonyl)-3-(1-methylpyrrolidin-3-yl)-1H-indole;
1- [(4,5-dichlorothien-2-yl) sulfonyl]-3-(1-methyl-pyrrolidin-3-yl)-1H-indole;
1-(2-bromophenylsulfonyl)-3-(1-methylpyrrolidin-3-yl)-1H-indole;
1-(4-iodophenylsulfonyl)-3-(1-methylpyrrolidin-3-yl)-1H-indole;
1-(2-iodophenylsulfonyl)-3-(1-methylpyrrolidin-3-yl)-1H-indole;
1-(4-aminophenylsulfonyl)-3-(1-benzylpyrrolidin-3-yl)-1H-indole;
3-(1-benzylpyrrolidin-3-yl)-1-(4-methylphenylsulfonyl)-1H-indole;
3-(1-benzylpyrrolidin-3-yl)-1-(3,4-dichlorophenyl-sulfonyl)-1H-indole;
3-(1-benzylpyrrolidin-3-yl)-1-(2-bromophenylsulfonyl)-1H-indole;
5-[3-(1-benzylpyrrolidin-3-yl)-indole-1-sulfonyl]-4-methyl-thiazol-2-ylamine;
3-(1-benzylpyrrolidin-3-yl)-1-[(5-bromothien-2-yl) sulfonyl]-1H-indole;
1-phenylsulfonyl-3-(1-methylpyrrolidin-3-yl)-1H-pyrrolo[2,3-b]pyridine;
1-phenylsulfonyl-3-(1-methylpyrrolidin-3-yl)-1H-indazole;
1-phenylsulfonyl-3-(1-methyl-2,5-dihydro-1H-pyrrol-3-yl)-1H-pyrrolo [2,3-b]pyridine;
1-phenylsulfonyl-3-(1-methyl-2,5-dihydro-1H -pyrrol-3-yl)-1H-indole;
1-(benzo[b]thioen-4-ylsulfonyl)-3-(1-methyl-pyrrolidin-3-yl)-1H-pyrrolo[2,3-b]pyridine;
1-(3-fluorophenylsulfonyl)-3-(1-methylpyrrolidin-3-yl)-1H-indazole;
1-(2,5-dichlorophenylsulfonyl)-3-(2,5-dihydro-1H-pyrrol-3-yl)-1H-pyrrolo[2,3-b]pyridine;
8-[3-(1-methyl-2,5-dihydro-1H-pyrrol-3-yl)indole-1-sulfonyl]-quinoline;
1-(benzo[b]thien-4-ylsulfonyl)-3-(1-benzyl-pyrrolidin-3-yl)-1H-pyrrolo[2,3-b]pyridine;
1-(3-fluoro-phenylsulfonyl)-3-(1-phenethyl-pyrrolidin-3-yl)-1H-indazole;
1-(2,5-dichlorophenylsulfonyl)-3-(1-ethyl-2,5-dihydro-1H-pyrrol-3-yl)-1H-pyrrolo[2,3-b]pyridine;
3-(1-methyl-2,5-dihydro-1H-pyrrol-3-yl)-1-(naphth-2-ylsulfonyl)-1H-indole;

and the pharmaceutically acceptable salts thereof.

8. A method for the treatment of a disorder of the central nervous system related to or affected by the 5-HT6 receptor selected from the group consisting of a mood disorder and a cognitive disorder in a patient in need thereof which comprises providing said patient with a therapeutically effective amount of a compound of formula I

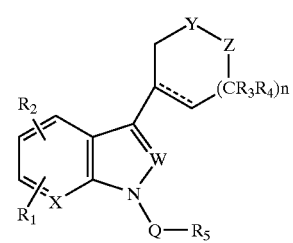

(I)

where in

Q is $SO_2$;

W is N or $CR_6$;

X is N or $CR_7$;

Y is $NR_8$ or $CR_9R_{10}$;

n is 0;

Z is $NR_{11}$ or $CR_{12}R_{13}$ with the proviso that when Y is $NR_8$ then Z must be $CR_{12}R_{13}$ and at least one of Y and Z must be $NR_8$ or $NR_{11}$;

$R_1$, $R_2$ and $R_7$ are each independently H, halogen, CN, $OCO_2R_{14}$, $CO_2R_{15}$, $CONR_{29}R_{30}$, $CNR_{16}NR_{17}R_{18}$, $SO_mR_{19}$, $NR_{20}R_{21}$, $OR_{22}$, $COR_{23}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_3$, $R_4$, $R_9$, $R_{10}$, $R_{12}$ and $R_{13}$ are each independently H or an optionally substituted $C_1$–$C_6$alkyl group;

$R_5$ is an optionally substituted $C_1$–$C_6$alkyl, aryl or heteroaryl group;

m is 0 or an integer of 1 or 2;

$R_6$ is H, halogen, or an optionally substituted $C_1$–$C_6$alkyl, $C_1$–$C_6$alkoxy, aryl or heteroaryl group;

R$_8$ and R$_{11}$ are each independently H, CNR$_{26}$NR$_{27}$R$_{28}$ or a C$_1$–C$_6$alkyl, C$_3$–C$_6$cycloalkyl, cycloheteralkyl, aryl or heteroaryl group each optionally substituted;

R$_{14}$, R$_{15}$, R$_{22}$ and R$_{23}$ are each independently H or an optionally substituted C$_1$–C$_6$alkyl, C$_2$–C$_6$alkenyl, C$_2$–C$_6$alkynyl, C$_3$–C$_6$cycloalkyl, cycloheteroalkyl, aryl or heteroaryl group;

R$_{16}$, R$_{17}$, R$_{18}$, R$_{20}$, R$_{21}$, R$_{26}$, R$_{27}$, R$_{28}$, R$_{29}$ and R$_{30}$ are each independently H or C$_1$–C$_4$alkyl;

R$_{19}$ is an optionally substituted C$_1$–C$_6$alkyl, aryl or heteroaryl group;

R$_{24}$ and R$_{25}$ are each independently H or an optionally substituted C$_1$–C$_6$alkyl, aryl or heteroaryl group; and ---- represents a single bond or a double bond; or
the stereoisomers thereof or the pharmaceutically acceptable salts thereof.

9. The method according to claim 8 wherein said disorder is schizophrenia.

10. The method according to claim 8 wherein said disorder is anxiety or depression.

11. The method according to claim 8 wherein said disorder is memory loss or attention deficit disorder.

12. A pharmaceutical composition which comprises a pharmaceutically acceptable carrier and an effective amount of a compound of formula I

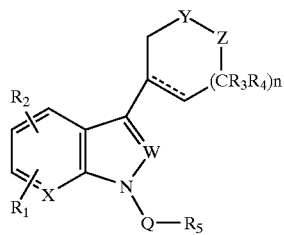

(I)

wherein

Q is SO$_2$;

W is N or CR$_6$;

X is N or CR$_7$;

Y is NR$_8$ or CR$_9$R$_{10}$;

n is 0;

Z is NR$_{11}$ or CR$_{12}$R$_{13}$ with the proviso that when Y is NR$_8$ then Z must be CR$_{12}$R$_{13}$ and at least one of Y and Z must be NR$_8$ or NR$_{11}$;

R$_1$, R$_2$ and R$_7$ are each independently H, halogen, CN, OCO$_2$R$_{14}$, CO$_2$R$_{15}$, CONR$_{29}$R$_{30}$, CNR$_{16}$NR$_{17}$R$_{18}$, SO$_m$R$_{19}$, NR$_{20}$R$_{21}$, OR$_{22}$, COR$_{23}$ or a C$_1$–C$_6$alkyl, C$_2$–C$_6$alkenyl, C$_2$–C$_6$alkynyl, C$_3$–C$_6$cycloalkyl, cycloheteroalkyl, aryl or heteroaryl group each optionally substituted;

R$_3$, R$_4$, R$_9$, R$_{10}$, R$_{12}$ and R$_{13}$ are each independently H or an optionally substituted C$_1$–C$_6$alkyl group;

R$_5$ is an optionally substituted C$_1$–C$_6$alkyl, aryl or heteroaryl group;

m is 0 or an integer of 1 or 2;

R$_6$ is H, halogen, or an optionally substituted C$_1$–C$_6$alkyl, C$_1$–C$_6$alkoxy, aryl or heteroaryl group;

R$_8$ and R$_{11}$ are each independently H, CNR$_{26}$NR$_{27}$R$_{28}$ or a C$_1$–C$_6$alkyl, C$_3$–C$_6$cycloalkyl, cycloheteralkyl, aryl or heteroaryl group each optionally substituted;

R$_{14}$, R$_{15}$, R$_{22}$ and R$_{23}$ are each independently H or an optionally substituted C$_1$–C$_6$alkyl, C$_2$–C$_6$alkenyl, C$_2$–C$_6$alkynyl, C$_3$–C$_6$cycloalkyl, cycloheteroalkyl, aryl or heteroaryl group;

R$_{16}$, R$_{17}$, R$_{18}$, R$_{20}$, R$_{21}$, R$_{26}$, R$_{27}$, R$_{28}$, R$_{29}$ and R$_{30}$ are each independently H or C$_1$–C$_4$alkyl;

R$_{19}$ is an optionally substituted C$_1$–C$_6$alkyl, aryl or heteroaryl group;

R$_{24}$ and R$_{25}$ are each independently H or an optionally substituted C$_1$–C$_6$alkyl, aryl or heteroaryl group; and ---- represents a single bond or a double bond; or
the stereoisomers thereof or the pharmaceutically acceptable salts thereof.

13. The composition according to claim 12 having a formula I compound wherein Y is NR$_8$; and X is CR$_7$.

14. The composition according to claim 12 having a formula I compound wherein X is CR$_7$; and Z is NR$_{11}$.

15. The composition according to claim 13 having a formula I compound wherein R$_5$ is an optionally substituted aryl group and ---- represents a single bond.

16. The composition according to claim 12 having a formula I compound selected from the group consisting of:

1-(4-fluorophenylsulfonyl)-3-(1-methyl-pyrrolidin-3-yl)-1H-indole;

1-(4-chlorophenylsulfonyl)-3-(1-methylpyrrolidin-3-yl)-1H-indole;

1-(naphth-2-ylsulfonyl)-3-(1-methylpyrrolidin-3-yl)-1H-indole;

1-(4-aminophenylsulfonyl)-3-(1-methylpyrrolidin-3-yl)-1H-indole;

1-(3,4-dimethoxyphenylsulfonyl)-3-(1-methylpyrrolidin-3-yl)-1H-indole;

1-(3,4-dichlorophenylsulfonyl)-3-(1-methylpyrrolidin-3-yl)-1H-indole;

1-[(4,5-dichlorothien-2-yl) sulfonyl]-3-(1-methyl-pyrrolidin-3-yl)-1H-indole;

1-(2-bromophenylsulfonyl)-3-(1-methylpyrrolidin-3-yl)-1H-indole;

1-(4-iodophenylsulfonyl)-3-(1-methylpyrrolidin-3-yl)-1H-indole;

1-(2-iodophenylsulfonyl)-3-(1-methylpyrrolidin-3-yl)-1H-indole;

1-(4-aminophenylsulfonyl)-3-(1-benzylpyrrolidin-3-yl)-1H-indole;

3-(1-benzylpyrrolidin-3-yl)-1-(4-methylphenylsulfonyl)-1H-indole;

3-(1-benzylpyrrolidin-3-yl)-1-(3,4-dichlorophenyl-sulfonyl)-1H-indole;

3-(1-benzylpyrrolidin-3-yl)-1-(2-bromophenylsulfonyl)-1H-indole;

5-[3-(1-benzylpyrrolidin-3-yl)-indole-1-sulfonyl]-4-methyl-thiazol-2-ylamine;

3-(1-benzylpyrrolidin-3-yl)-1-[(5-bromothien-2-yl) sulfonyl]-1H-indole;

1-phenylsulfonyl-3-(1-methylpyrrolidin-3-yl)-1H-pyrrolo[2,3-b]pyridine;

1-phenylsulfonyl-3-(1-methylpyrrolidin-3-yl)-1H-indazole;

1-phenylsulfonyl-3-(1-methyl-2,5-dihydro-1H-pyrrol-3-yl)-1H-pyrrolo[2,3-b]pyridine;

1-phenylsulfonyl-3-(1-methyl-2,5-dihydro-1H-pyrrol-3-yl)-1H-indole;

1-(benzo[b]thioen-4-ylsulfonyl)-3-(1-methyl-pyrrolidin-3-yl)-1H-pyrrolo[2,3-b]pyridine;

1-(3-fluorophenylsulfonyl)-3-(1-methylpyrrolidin-3-yl)-1H-indazole;

1-(2,5-dichlorophenylsulfonyl)-3-(2,5-dihydro-1H-pyrrol-3-yl)-1H-pyrrolo[2,3-b]pyridine;

8-[3-(1-methyl-2,5-dihydro-1H-pyrrol-3-yl)indole-1-sulfonyl]-quinoline;

1-(benzo[b]thien-4-ylsulfonyl)-3-(1-benzyl-pyrrolidin-3-yl)-1H-pyrrolo[2,3-b]pyridine;

1-(3-fluoro-phenylsulfonyl)-3-(1-phenethyl-pyrrolidin-3-yl)-1H-indazole;

1-(2,5-dichlorophenylsulfonyl)-3-(1-ethyl-2,5-dihydro-1H-pyrrol-3-yl)-1H-pyrrolo[2,3-b]pyridine;

3-(1-methyl-2,5-dihydro-1H-pyrrol-3-yl)-1-(naphth-2-ylsulfonyl)-1H-indole;

the pharmaceutically acceptable salts thereof.

17. A process for the preparation of a compound of formula If

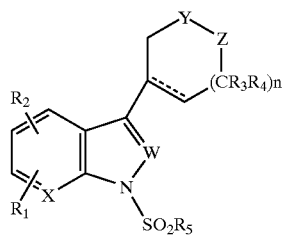

(If)

wherein

W is N or $CR_6$;

X is N or $CR_7$;

Y is $NR_8$ or $CR_9R_{10}$;

n is 0;

Z is $NR_{11}$ or $CR_{12}R_{13}$ with the proviso that when Y is $NR_8$ then Z must be $CR_{12}R_{13}$ and at least one of Y and Z must be $NR_8$ or $NR_{11}$;

$R_1$, $R_2$ and $R_7$ are each independently H, halogen, CN, $OCO_2R_{14}$, $CO_2R_{15}$, $CONR_{29}R_{30}$, $CONR_{29}R_{30}$, $CNR_{16}NR_{17}R_{18}$, $SO_mR_{19}$, $NR_{20}R_{21}$, $OR_{22}$, $COR_{23}$ or a $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group each optionally substituted;

$R_3$, $R_4$, $R_9$, $R_{10}$, $R_{12}$ and $R_{13}$ are each independently H or an optionally substituted $C_1$–$C_6$alkyl group;

$R_5$ is an optionally substituted $C_1$–$C_6$alkyl, aryl or heteroaryl group;

m is 0 or an integer of 1 or 2;

$R_6$ is H, halogen, or an optionally substituted $C_1$–$C_6$alkyl, $C_1$–$C_6$alkoxy, aryl or heteroaryl group;

$R_8$ and $R_{11}$ are each independently H, $CNR_{26}NR_{27}R_{28}$ or a $C_1$–$C_6$alkyl, $C_3$–$C_6$cycloalkyl, cycloheteroalkyl, aryl or heteroaryl group each optionally substituted;

$R_{14}$, $R_{15}$, $R_{22}$ and $R_{23}$ are each independently H or an optionally substituted $C_1$–$C_6$alkyl, $C_2$–$C_6$alkenyl, $C_2$–$C_6$alkynyl, $C_3$–$C_6$cycloalkyl, cycloheteroalkyl, aryl or heteroaryl group;

$R_{16}$, $R_{17}$, $R_{18}$, $R_{20}$, $R_{21}$, $R_{26}$, $R_{27}$, $R_{28}$, $R_{29}$ and $R_{30}$ are each independently H or $C_1$–$C_4$alkyl;

$R_{19}$ is an optionally substituted $C_1$–$C_6$alkyl, aryl or heteroaryl group; and ---- represents a single bond or a double bond which process comprises reacting a compound of formula IVa

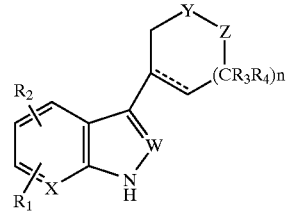

(IVa)

wherein W, X, Y, Z, n, $R_1$, $R_2$, $R_3$ and $R_4$ are as defined above with a sulfonyl chloride, $R_5SO_2Cl$, wherein $R_5$ is defined above in the presence of a base.

* * * * *